(12) United States Patent
Ini et al.

(10) Patent No.: US 7,842,717 B2
(45) Date of Patent: Nov. 30, 2010

(54) DNT-MALEATE AND METHODS OF PREPARATION THEREOF

(75) Inventors: Santiago Ini, Haifa (IL); Anita Liberman, Tel-Aviv (IL); Mili Abramov, Givataim (IL); Tamas Koltai, Netanya (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/525,336

(22) Filed: Sep. 21, 2006

(65) Prior Publication Data

US 2007/0185192 A1 Aug. 9, 2007

Related U.S. Application Data

(60) Provisional application No. 60/719,880, filed on Sep. 22, 2005, provisional application No. 60/761,583, filed on Jan. 23, 2006, provisional application No. 60/771,069, filed on Feb. 6, 2006.

(51) Int. Cl.
*A61K 31/381* (2006.01)
*C07D 333/20* (2006.01)

(52) U.S. Cl. .................................... 514/438; 549/75
(58) Field of Classification Search ................. 514/438; 549/75
See application file for complete search history.

(56) References Cited

U.S. PATENT DOCUMENTS

| 4,314,081 | A | 2/1982 | Molloy et al. |
| 5,023,269 | A | 6/1991 | Robertson et al. |
| 5,362,886 | A | 11/1994 | Berglund |
| 5,491,243 | A | 2/1996 | Berglund |
| 5,508,276 | A | 4/1996 | Anderson et al. |
| 6,541,668 | B1 | 4/2003 | Kjell et al. |
| 2005/0197503 | A1 | 9/2005 | Schiffers et al. |
| 2006/0063943 | A1 | 3/2006 | Sakai et al. |
| 2006/0194869 | A1 | 8/2006 | Ini et al. |
| 2006/0270861 | A1 | 11/2006 | Ini et al. |
| 2007/0167636 | A1 | 7/2007 | Butchko et al. |

FOREIGN PATENT DOCUMENTS

| EP | 0 273 658 | 7/1988 |
| EP | 0 457 559 | 11/1991 |
| EP | 0 654 264 | 5/1995 |
| EP | 1 506 965 | 2/2005 |
| WO | WO 00/61540 | 10/2000 |
| WO | WO 03/070720 A1 | 8/2003 |
| WO | WO 2004/031168 A | 4/2004 |
| WO | WO 2004/056795 | 7/2004 |
| WO | WO 2005/108386 A1 | 11/2005 |
| WO | WO 2006/027798 A2 | 3/2006 |
| WO | WO 2006/045255 | 5/2006 |
| WO | WO 2006/096809 | 9/2006 |
| WO | WO 2006/099433 | 9/2006 |
| WO | WO 2006/126213 | 11/2006 |
| WO | WO 2007/077580 | 7/2007 |
| WO | WO 2007/096707 | 8/2007 |

OTHER PUBLICATIONS

Deeter et al., Tetrahed. Letts. (1990), vol. 31(49), pp. 7101-7104.*
Wheeler W. J., et al, "An Asymmetric Synthesis of Duloxetine Hydrochloride, a Mixed Uptake Inhibitor of Serotonin and Norepinephrine, and its C-14 Labeled Isotopomers", *J. Label .Cpds. Radiopharm*, 36(3): 213-223 (1995).
Valenta, V. et al., "Potential Antidepressants: 3-aryl-3-(arylthio)propylamines as selective inhibitors of 5-hydroxytryptamine reuptake in the brain", *Collection of Czechoslovak Chemical Communications*, 56(7): 1525-1533 (1991).
Abdel-Monem, et al., "N-Demethylation of Morphine and Structurally Related Compounds With Chloroformate Esters", *J. Med. Chem.*, 1972, pp. 208-210, vol. 15, No. 2.
Deeter, et al., "Asymmetric Synthesis and Absolute Stereochemistry of LY248686", *Tetrahedron Letters*, 1990, pp. 7101-7104, vol. 31, No. 49.
Kamal, et al., "Chemoenzymatic Synthesis of Duloxetine and Its Enantiomer: Lipase-Catalyzed Resolution of 3-Hydroxy-3-(2-Thienyl) Propanenitrile", *Tetrahedron Letters*, 2003, pp. 4783-4787, vol. 44, No. 25.
Kometani, et al., "On the Cleavage of Tertiary Amines With Ethyl Chloroformate", *Chem. Pharm. Bull.*, 1976, pp. 342-349, vol. 24, No. 2.
Fujima, Yoshito et al., "Synthesis of (S)-3-(N-Methylamino)-1-(2-thienyl)propan-1-ol: Revisiting Eli Lilly's Resolution-Racemization-Recycle Synthesis of Duloxetine for Its Robust Processes," *Organic Process Research & Development*, 10(5): 905-913 (2006).
Sakai, K. et al., "Resolution of 3-(methylamino)-1-(2-thienyl)propan-1-ol, a new key intermediate for duloxetine, with (S)-mandelic acid," *Tetrahedron: Asymmetry*, 14(12): 1631-1636 (2003).
L.A. Sorbera, et al., "Duloxetine Oxalate", *Drugs of the Future*, vol. 25, No. 9, pp. 907-916, (2000).

* cited by examiner

*Primary Examiner*—Taofiq A Solola
(74) *Attorney, Agent, or Firm*—Kenyon & Kenyon LLP (57) ABSTRACT

(S)-N,N-Dimethyl-3-(1-naphthalenyloxy)-3-(2-thienyl)propanamine maleate (DNT-maleate) and polymorphs of DNT-maleate, compositions of DNT-maleate and its polymorphs, processes for the preparation of DNT-maleate and its polymorphs, and processes for the preparation of duloxetine hydrochloride from DNT-maleate are provided.

15 Claims, 2 Drawing Sheets

Fig. 1 – Form Ma1

Fig. 2 – Form Ma2

Fig. 3 – Form Ma3

DNT-MALEATE AND METHODS OF PREPARATION THEREOF

CROSS-REFERENCE TO RELATED APPLICATIONS

The present application claims the benefit of the following U.S. Provisional Patent Application No.: 60/719,880 filed Sep. 22, 2005, 60/761,583 filed Jan. 23, 2006 and 60/771,069 filed Feb. 6, 2006. The contents of which are incorporated herein by reference.

FIELD OF THE INVENTION

The invention is directed to an intermediate for the synthesis of duloxetine. In particular, the invention is directed to the duloxetine intermediate DNT-maleate, to the solid state chemistry of DNT-maleate, and to processes for preparing DNT-maleate and to converting DNT-maleate into duloxetine HCl.

BACKGROUND OF THE INVENTION

Duloxetine hydrochloride (duloxetine HCl) is a dual reuptake inhibitor of the neurotransmitters serotonin and norepinephrine. It is used for the treatment of stress urinary incontinence (SUI), depression, and pain management. Duloxetine hydrochloride is known by the chemical name (S)-(+)-N-methyl-3-(1-naphthalenyloxy)-3-(2-thienyl) propanamine hydrochloric acid salt, and has the following structure.

Duloxetine, as well as processes for its preparation, is disclosed in U.S. Pat. No. 5,023,269. EP Patent No. 457559 and U.S. Pat. Nos. 5,491,243 and 6,541,668 also provide synthetic routes for the preparation of duloxetine. U.S. Pat. No. 5,023,269 discloses preparing duloxetine by reacting (S)-(-)-N,N-Dimethyl-3-(2-thienyl)-3-hydroxypropanamine with fluoronaphtalene (Stage a), followed by demethylation with phenyl chloroformate or trichloroethyl chloroformate (Stage b) and basic hydrolysis (Stage c), according the following scheme.

R = Phenyl, trichloroethyl

The conversion of duloxetine to its hydrochloride salt in ethyl acetate (Stage d) is described in U.S. Pat. No. 5,491,243 and in Wheeler, W. J., et al, *J. Label. Cpds. Radiopharm*, 1995, 36, 312.

As illustrated in the above scheme, DNT is an intermediate in the preparation of duloxetine. DNT has an N,N-dimethyl group instead of a secondary amine.

U.S. Pat. No. 5,023,269 describes the preparation of DNT-oxalate from DNT. See Example 1.

The oxalate salt of U.S. Pat. No. 5,023,269 is problematic for use on an industrial process. Oxalic acid has to be used to prepare the oxalate. Oxalic acid is highly toxic. Therefore, there is a need in the art to prepare duloxetine HCl with a relative high purity with a process that is suitable for industrial scale.

Stereochemical purity is of importance in the field of pharmaceuticals, where many of the most prescribed drugs exhibit chirality, and the two isomers exhibit different potency. Furthermore, optical purity is important since certain isomers may actually be deleterious rather than simply inert. Therefore, there is a need to obtain the desired enantiomer of duloxetine HCl in high enantiomeric purity.

A composition of DNT is often contaminated with enantiomeric impurity. This enantiomeric impurity generally carries over to the final pharmaceutical product, i.e., duloxetine HCl. The present Applicants have found out that formation of the oxalate salt as carried out in EP Patent No. 457559 does not reduce the amount of the enantiomeric impurity (enantiomer R). There is a need in the art for a process that reduces the quantity of enantiomer R present in DNT.

SUMMARY OF THE INVENTION

In one embodiment, the invention provides a compound (DNT-maleate) having the MD following formula:

In another embodiment the invention provides a process for preparing a pharmaceutically acceptable salt of duloxetine, comprising combining DNT, a solvent selected from the group consisting of $C_{1-8}$ alcohols, $C_{3-7}$ esters, $C_{3-8}$ ethers, $C_{3-7}$ ketones, $C_{6-12}$ aromatic hydrocarbons, acetonitrile, water and mixtures thereof with maleic acid to form a reaction mixture, precipitating DNT-maleate from the reaction mixture, optionally recrystallizing the DNT maleate from ethyl acetate, converting the DNT maleate to DNT, converting the DNT to duloxetine, and converting the duloxetine to the pharmaceutically acceptable salt of duloxetine.

In another embodiment, the invention provides a crystalline form of DNT-maleate:

characterized by a powder XRD pattern with peaks at about 9.4°, 14.0°, 18.7°, 23.30°, and 24.9° 2θ±0.2° 2θ.

In another embodiment, the invention provides a crystalline form of DNT-maleate:

characterized by a powder XRD pattern with peaks at about 14.4°, 18.5°, 23.1°, 27.2°, and 31.3° 2θ±0.2° 2θ.

In another embodiment, the invention provides a crystalline form of DNT maleate:

characterized by a powder XRD pattern with peaks at about 9.4°, 18.7°, 23.4°, and 25.3° 2θ±0.2° 2θ.

In another embodiment, the invention provides a process for preparing a pharmaceutically acceptable salt of duloxetine, comprising combining DNT, a solvent selected from the group consisting of $C_{1-8}$ alcohols, $C_{3-7}$ esters, $C_{3-8}$ ethers, $C_{3-7}$ ketones, $C_{6-12}$ aromatic hydrocarbons, acetonitrile, water and mixtures thereof with maleic acid to form a reaction mixture, precipitating DNT-maleate from the reaction mixture, recrystallizing the DNT maleate from ethyl acetate, converting the DNT maleate to DNT, converting the DNT to duloxetine, and converting the duloxetine to the pharmaceutically acceptable salt of duloxetine. preparing a pharmaceutically acceptable salt of duloxetine, comprising combining DNT, a solvent selected from the group consisting of $C_{1-8}$ alcohols, $C_{3-7}$ esters, $C_{3-8}$ ethers, $C_{3-7}$ ketones, $C_{6-12}$ aromatic hydrocarbons, acetonitrile, water and mixtures thereof with maleic acid to form a reaction mixture, precipitating DNT-maleate from the reaction mixture, recrystallizing the DNT maleate from ethyl acetate, converting the DNT maleate to DNT, converting the DNT to duloxetine, and converting the duloxetine to the pharmaceutically acceptable salt of duloxetine.

DETAILED DESCRIPTION OF THE INVENTION

The present invention provides DNT-maleate, which can be represented by the formula $C_{23}H_{25}NO_5S$ and the structure:

DNT-maleate is preferably isolated as a solid, and, more preferably as a crystal. The use of DNT-maleate as an intermediate salt for preparation of DNT, which is an intermediate of duloxetine, allows for obtaining such hydrochloride salt in relatively high purity without many of the drawbacks of the oxalate salt.

Use of the DNT-maleate salt provides an enantiomeric cleaning effect not observed with the oxalate salt. The cleaning effect results from the process of obtaining DNT-maleate which produces a greater ratio of the S enantiomer relative to the R enantiomer, than was present in the DNT starting material.

DNT-maleate can be characterized by data selected from: $^1$H NMR (400 MHz, CDCl3 d6) δ(ppm): 8.32 (d, J=8.3 Hz, 1H), 7.82 (d, J=8.0 Hz, 1H), 7.55 (m, 2H), 7.46 (d, J=8.2 Hz, 1H), 7.31 (m, 2H), 7.14 (d, J=3.4 Hz, 1H), 6.98 (t, J=4.3 Hz, 1H), 6.87 (d, J=7.7 Hz, 1H), 6.31 (s, 2H), 5.85 (t, J=6.1 Hz, 1H), 3.16 (m, 2H), 2.83 (s, 6H), 2.69 (m, 1H), 2.57 (m, 1H); 13C {1H}NMR (100 MHz): δ 171.0, 153.8, 144.1, 137.0, 136.0, 129.1, 128.5, 128.0, 127.2, 127.1, 127.0, 126.9, 123.1, 122.8, 108.6, 74.8, 55.9, 44.35, 34.9; and FAB MS: m/z 312 ([M−H]+, 100%).

The present invention also provides a process for preparing DNT maleate. DNT maleate may be prepared by combining DNT and maleic acid to create a reaction mixture. DNT maleate forms in such reaction mixture through contact of DNT with maleic acid.

In one embodiment, a solution or a suspension of DNT in a solvent is combined with maleic acid to form a reaction mixture, followed by recovery of the DNT-maleate salt from the mixture. The maleic acid may be either added as a solid or as a solution or suspension in an organic solvent. The organic solvent present in the reaction mixture is preferably selected from the group consisting of $C_{1-8}$ alcohols, $C_{3-7}$ esters, $C_{3-8}$ ethers, $C_{3-7}$ ketones, $C_{6-12}$ aromatic hydrocarbons, acetonitrile, water and mixtures thereof. Preferably, the solvent is acetone, n-BuOH, ethyl acetate, MTBE, toluene or water. More preferably, the solvent is at ethyl acetate, acetone, or n-BuOH.

In one embodiment, DNT, maleic acid and at least one solvent are combined to form a reaction mixture at about room temperature. The amount of maleic acid present in such reaction mixture is preferably to the point of saturation. DNT maleate then precipitates out of such mixture. Such precipitation may occur on its own or be induced. The reaction mixture may be stirred before, during or after precipitation.

In another embodiment, maleic acid and DNT in a solvent are heated to form a reaction mixture. Heating may be carried out from about room temperature to about the reflux temperature of the solvent. DNT maleate forms in the reaction mixture. The reaction mixture may then be cooled to facilitate precipitation. Cooling is generally carried to a temperature of about 50° C. or less, preferably about room temperature, to facilitate precipitation. The reaction mixture may be stirred before, during or after precipitation.

The above embodiments, with or without heating, may be carried out without a solvent. In this method, DNT is used both as a reagent and a solvent; Maleic acid and DNT are combined to form a reaction mixture followed by precipitation.

The resulting precipitate from any of the above embodiments may be recovered by conventional techniques, such as filtration. The precipitate may be dried under ambient or reduced pressure, or elevated temperature. In one embodiment, the precipitate is dried at room temperature at a pressure of less than about 100 mmHg.

The DNT-maleate of the invention can be prepared in different polymorphic forms. Polymorphism, the occurrence of different crystal forms, is a property of some molecules and molecular complexes. A single molecule, such as DNT-maleate may give rise to a variety of crystalline forms having distinct crystal structures and physical properties like melting point, X-ray diffraction pattern, infrared absorption fingerprint, and solid state NMR spectrum. One crystalline form may give rise to thermal behavior different from that of another crystalline form. Thermal behavior can be measured in the laboratory by such techniques as capillary melting point, thermogravimetric analysis ("TGA"), and differential scanning calorimetry ("DSC"), which have been used to distinguish polymorphic forms.

The difference in the physical properties of different crystalline forms results from the orientation and intermolecular interactions of adjacent molecules or complexes in the bulk solid. Accordingly, polymorphs are distinct solids sharing the same molecular formula, yet having distinct physical properties that can be advantageous in certain applications compared to other crystalline forms of the same compound or complex. Therefore, processes for the preparation of polymorphic forms of DNT-maleate are desirable.

Figure 1:
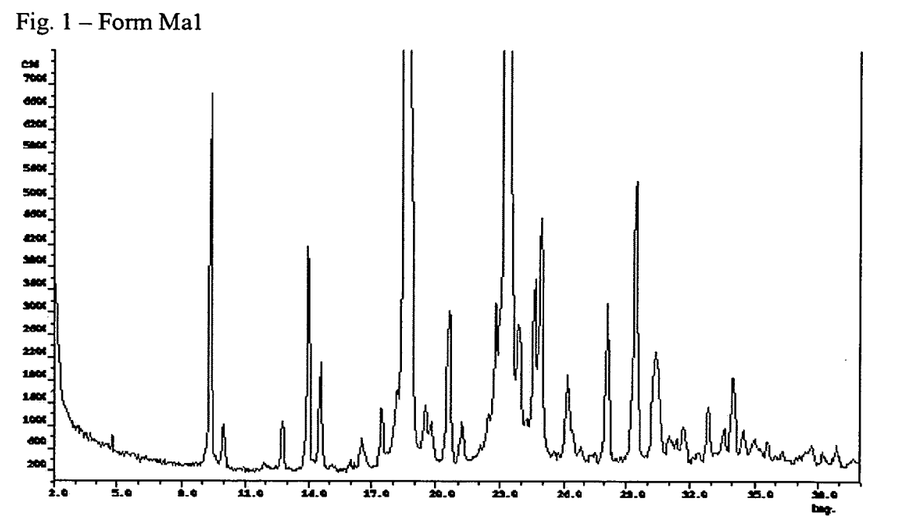
FIG. 1 illustrates the powder X-ray diffraction pattern for DNT-maleate Form Ma1.

One such crystalline form of DNT-maleate, herein defined as Form Ma1, is characterized by a powder XRD pattern with peaks at about 9.4°, 14.0°, 18.7°, 23.3°, and 24.9° 2θ±0.2° 2θ. The crystalline Form Ma1 may be further characterized by X-ray powder diffraction peaks at about 20.6°, 24.6°, and 29.4° 2θ±0.2° 2θ. DNT-maleate Form Ma1 can also be characterized by an X-ray powder diffraction pattern substantially as depicted in FIG. 1.

Form Ma1 may be prepared by precipitation from a $C_3$-$C_7$ ketone, preferably acetone. This process is preferably carried out at about room temperature. In this embodiment, DNT, maleic acid and the ketone are combined to form a mixture, followed by recovery of the DNT maleate. Generally, maleic acid is added to a solution of DNT in the ketone. The maleic acid may also be added as a solution in the ketone to a solution of the DNT in the ketone. The DNT maleate precipitates from the reaction mixture. The reaction mixture may be stirred before, during or after precipitation. The precipitate may be recovered by conventional techniques, such as filtration. The precipitate may be dried under ambient or reduced pressure, or elevated temperature. In one embodiment, the precipitate is dried at room temperature at a pressure of less than about 100 mmHg.

Figure 2:
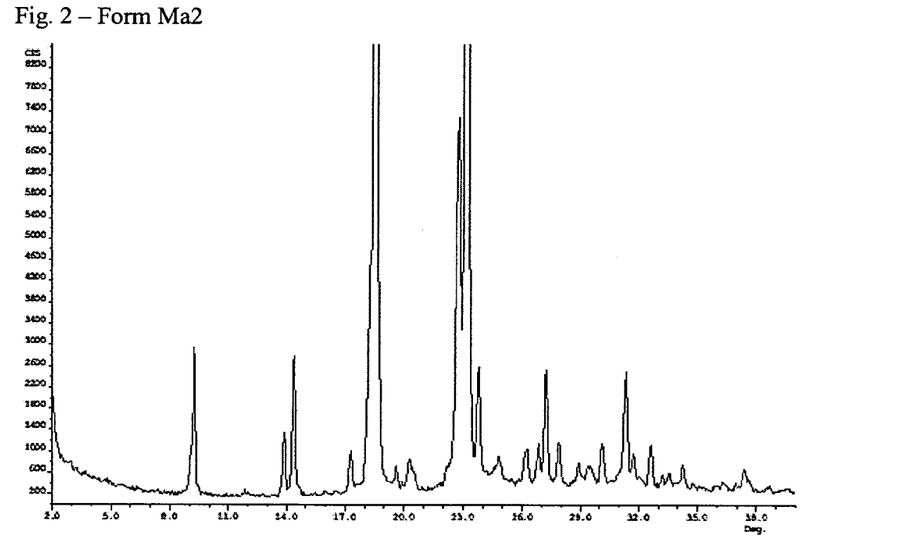
FIG. 2 illustrates the powder X-ray diffraction pattern for DNT-maleate Form Ma2.

Another crystalline form of DNT-maleate, herein defined as Form Ma2, is characterized by a powder XRD pattern with peaks at about 14.4°, 18.5°, 23.1°, 27.2°, and 31.3° 2θ±0.2° 2θ. The crystalline Form Ma2 may be further characterized by X-ray powder diffraction peaks at about 13.9°, 20.3°, and 26.3° 2θ±0.2° 2θ. DNT-maleate Form Ma2 can also be characterized by an X-ray powder diffraction pattern substantially as depicted in FIG. 2.

Form Ma2 may be prepared by precipitation from a wide range of solvents including $C_3$-$C_7$ ester, $C_1$-$C_8$ alcohol, $C_3$-$C_8$ ether, water or mixtures thereof, preferably n-butyl alcohol, ethyl acetate, MTBE, water and mixtures thereof.

In one embodiment, DNT, maleic acid and at least one solvent listed above are combined to form a reaction mixture at about room temperature. The amount of maleic acid present in such reaction mixture is preferably to the point of saturation. DNT maleate Form Ma2 then precipitates out of such mixture. Such precipitation may occur on its own or be induced. The reaction mixture may be stirred before, during or after precipitation.

In another embodiment, maleic acid and DNT in a solvent are heated to form a reaction mixture. The amount of maleic acid present in such reaction mixture is preferably to the point of saturation. Heating may be carried out from about room temperature to about the reflux temperature of the solvent. DNT maleate forms in the reaction mixture. The reaction mixture may then be cooled to facilitate precipitation of the DNT maleate Form Ma2. Cooling is generally carried to a temperature of about 50° C. or less, preferably about room temperature, to facilitate precipitation. The reaction mixture may be stirred before, during or after precipitation.

The resulting Form Ma2 precipitate may be recovered by conventional techniques, such as filtration. The precipitate may be dried under ambient or reduced pressure, or elevated temperature. In one embodiment, the precipitate is dried at room temperature at a pressure of less than about 100 mmHg.

Figure 3:
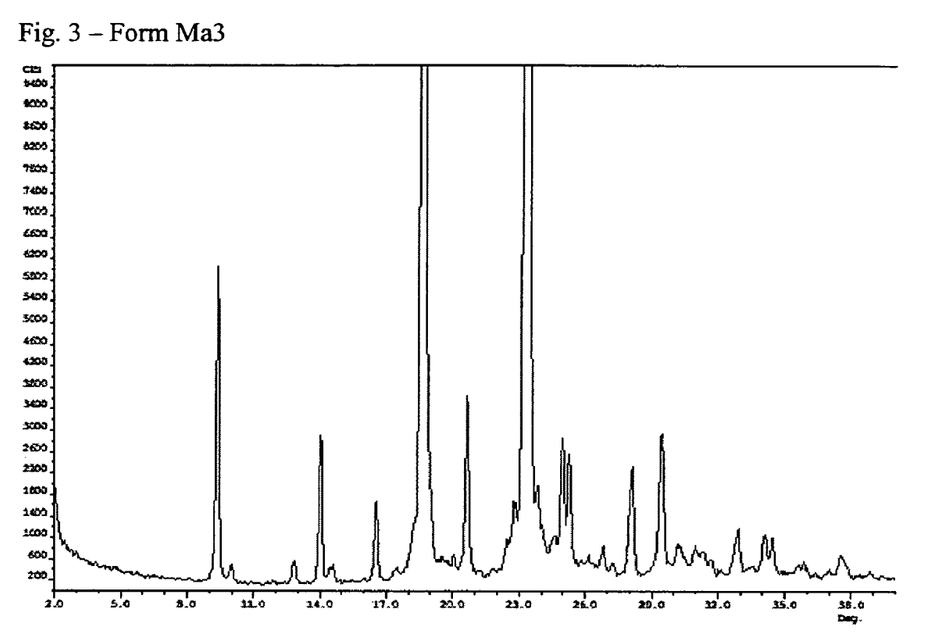
FIG. 3 illustrates the powder X-ray diffraction pattern for DNT-maleate Form Ma3.

A further crystalline form of DNT-maleate, herein defined as Form Ma3, is characterized by a powder XRD pattern with peaks at about 9.4°, 18.7°, 23.4°, and 25.3° 2θ±0.2° 2θ. The crystalline Form Ma3 may be further characterized by X-ray powder diffraction peaks at about 14.0°, 20.6°, 24.9°, 28.1°, and 29.5° 2θ±0.2° 2θ. DNT-maleate Form Ma3 can also be characterized by an X-ray powder diffraction pattern substantially as depicted in FIG. 3.

Form Ma3 may be prepared by precipitation from a heated $C_3$-$C_7$ ketone reaction mixture, preferably acetone. In this embodiment, DNT, maleic acid and the ketone are combined to form a mixture. Generally, maleic acid and DNT in the ketone are heated, followed by cooling to facilitate precipitation. The temperature for heating is generally about room temperature to about reflux temperature of the solvent. The reaction mixture may be stirred before, during or after precipitation. Cooling is generally carried to a temperature of less than about 50° C., preferably less than about room temperature, most preferably, at 4° C. The resulting precipitate may be recovered by conventional techniques, such as filtration. The precipitate may be dried under ambient or reduced pressure, or elevated temperature. In one embodiment, the precipitate are dried at room temperature at a pressure of less than about 100 mmHg.

Preferably, the DNT-maleate resulting from any of the above processes is present in a composition (such as a batch) having a polymorphic purity of at least about 10 percent by weight, more preferably, at least about 25 percent by weight, and most preferably at least about 50 percent by weight of a single crystalline form.

Preparation of the maleate salt can also lower the amount of the undesired R-enantiomer present in DNT. Such reduction in the level of undesired R-enantiomer can be calculated according to the following formula:

$$\left(1 - \frac{\% \ R_{DNT-Maleate}}{\% \ R_{DNT}}\right) \times 100$$

Preferably the molar amount of the R-enantiomer of DNT-maleate, compared to the starting material, is less than about 50 percent, more preferably less than about 20 percent and even more preferably less than about 4 percent of the molar amount present in such starting material.

Repetitions of the processes for preparation of DNT-maleate can increase the enantiomeric purity even further, preferably to an undetectable amount of the undesired R-enantiomer. In other words, the process may further comprise combining DNT-maleate with a base, combining the DNT-base with maleic acid to form a reaction mixture, precipitating DNT-maleate from the reaction mixture, and recovering the DNT-maleate.

To decrease the level of the R-enantiomer of DNT-maleate even further, the DNT-maleate prepared by the processes of the present invention may be crystallized from one or more polar solvents, such as $C_{1-8}$ alcohols, e.g., n-butanol, $C_{3-7}$ esters, e.g., ethyl acetate, water, and mixtures thereof. Preferably, the DNT-maleate of the invention is crystallized from ethyl acetate. The crystallization may be performed by dissolving DNT-maleate in the organic solvent, preferably at a temperature of about room temperature to about reflux temperature, followed by cooling. The obtained DNT-maleate is recovered by any method known in the art, such as filtering, and may be further washed and dried.

In one embodiment of the present invention, successive crystallization from ethyl acetate is carried out until the enantiomeric impurity is no longer detectable. A solvent as listed above may be used instead of ethyl acetate. The DNT-maleate of the present invention preferably contains less than about 50%, more preferably less than about 15%, even more preferably less than about 5%, and even more preferably less than about 0.04% of enantiomeric impurity. Most preferably such impurity is undetectable by HPLC.

The DNT-maleate of the invention, including Form Ma1, Form Ma2 and Form Ma3, will generally have a maximal particle size of less than about 500 μm, preferably less than about 300 μm, more preferably less than about 200 μm, and most preferably less than about 100 μm. A particularly preferred crystalline Form Ma3 of DNT-maleate has a maximal particle size of less than about 50 µm. The particle size of DNT-maleate crystalline forms may be measured by methods including, but not limited to sieves, sedimentation, electrozone sensing (coulter counter), microscopy, and Low Angle Laser Light Scattering (LALLS).

The DNT-maleate of the present invention is useful as an intermediate in the preparation of pharmaceutically salts of duloxetine, particularly the hydrochloride salt. The conversion can be carried out by combining DNT-maleate, water, a base such as ammonium hydroxide, and toluene to obtain a two phase system, separating the organic phase containing DNT and toluene, and converting the DNT to duloxetine HCl. The DNT-maleate used in this process is preferably the DNT-maleate prepared as described above. As such, it has a low content of the R-enantiomer, and, therefore, the duloxetine HCl obtained from the DNT-maleate of the invention also has a decreased R-enantiomer content.

The conversion of DNT to a pharmaceutically acceptable salt of duloxetine may be performed by any method known in the art, such as the one described in U.S. Pat. No. 5,023,269 or in co-pending U.S. patent application Ser. No. 11/318,365, filed on Dec. 23, 2005, for making duloxetine HCl. Preferably, the conversion is performed by dissolving DNT in an organic solvent, and combining it with an alkyl haloformate. That step will yield duloxetine alkyl carbamate, which can be combined with an organic solvent and a base, to yield duloxetine. The duloxetine may then be converted to a pharmaceutically acceptable salt. More preferably, the conversion is performed by dissolving DNT in a water immiscible organic solvent; adding alkyl chloroformate at a temperature of about 5° C. to less than about 80° C. to obtain duloxetine alkyl carbamate, combining the duloxetine alkyl carbamate with an organic solvent and a base; maintaining the reaction mixture at reflux temperatures for at least 1 to 3 hours; cooling, and adding water and an additional amount of an organic solvent; recovering duloxetine; combining the duloxetine with a solvent; adding hydrochloric acid until a pH of about 3 to about 4 is obtained; maintaining the reaction mixture to obtain a solid residue; and recovering duloxetine HCl.

Pharmaceutical compositions can be made using the pharmaceutically acceptable salts of duloxetine from the processes described above. A pharmaceutical composition may comprise a pharmaceutically acceptable salts of duloxetine from the processes described above, and a pharmaceutically acceptable excipient. Preferably, a pharmaceutical composition can be made by combining the duloxetine HCl produced by the above method with a pharmaceutically acceptable excipient. These pharmaceutical compositions contain less than about 50%, more preferably less than about 15%, even more preferably less than about 5%, and even more preferably less than about 0.04% of enantiomeric impurity. Most preferably such impurity is undetectable by HPLC.

In addition to the active ingredient(s), the pharmaceutical compositions of the present invention contain one or more excipients or adjuvants. Selection of excipients and the amounts to use may be readily determined by the formulation scientist based upon experience and consideration of standard procedures and reference works in the field.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease the release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be died using any pharmaceutically acceptable colorant to improve their appearance and/or facilitate patient identification of the product and unit dosage level.

In liquid pharmaceutical compositions of the present invention, the active ingredient and any other solid excipients are suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxy toluene, butylated hydroxyanisole, and ethylenediamine tetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate, or sodium acetate.

Selection of excipients and the amounts used may be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages may be conveniently presented in unit dosage form and prepared by any of the methods well known in the pharmaceutical arts.

Dosage forms include solid dosage forms like tablets, powders, capsules, suppositories, sachets, troches, and losenges, as well as liquid syrups, suspensions, and elixirs.

The dosage form of the present invention may be a capsule containing the composition, preferably a powdered or granulated solid composition of the invention, within either a hard or soft shell. The shell may be made from gelatin, and, optionally, contain a plasticizer such as glycerin and sorbitol, and an opacifying agent or colorant.

The active ingredient and excipients may be formulated into compositions and dosage forms according to methods known in the art.

A composition for tableting or capsule filling can be prepared by wet granulation. In wet granulation, some or all of the active ingredients and excipients in powder form are blended, and then further mixed in the presence of a liquid, typically water, that causes the powders to clump into granules. The granulate is screened and/or milled, dried, and then screened and/or milled to the desired particle size. The granulate may then be tableted or other excipients may be added prior to tableting, such as a glidant and/or a lubricant.

A tableting composition can be prepared conventionally by dry blending. For example, the blended composition of the actives and excipients may be compacted into a slug or a sheet, and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The following non-limiting examples are merely illustrative of the preferred embodiments of the present invention, and are not to be construed as limiting the invention, the scope of which is defined by the appended claims.

EXAMPLES

Instruments

X-Ray powder diffraction (XRD) data was obtained using a Scintag X-ray powder diffractometer model X'TRA equipped with a Cu-tube solid state detector. A round standard aluminum sample holder with rough zero background quartz plate with a cavity of 25 (diameter)×0.5 mm (depth) was used. The scanning parameters included: range: 2° to 40° 2θ; scan mode: continuous scan; step size: 0.05°; and a rate of 5°/minute.

HPLC Method for Measuring Enantiomeric Purity:

| | |
|---|---|
| Column: | Diacel Chiral OD 250 × 4.65 μm |
| Eluent: | Hexane (900 ml): IPA (100 ml): DEA (2 ml) |
| Flow: | 1 ml/minute |
| Detection: | 230 nm |
| Sample conc: | 0.5 mg/ml |
| Sample vol: | 100 μl |
| Column temp: | 20° C. |
| Detection limit: | 0.02% |

Preparation of DNT Maleate

Example 1

A solution of 7.45 g maleic acid in 50 ml acetone was added to a solution of 20 g DNT in 25 ml of acetone at 25° C., and stirred at the same temperature for one hour. The resulting solid was filtered off, washed with 10 ml of acetone, and dried in a vacuum oven (10 mm Hg) at room temperature for 48 hours, resulting in 18.65 g of DNT maleate (chemical yield: 68%). The product was analyzed by XRD and found to be Form Ma1.

Examples 2-5

Maleic acid (1.5 g) was added to a solution of 4 g of DNT (2.30% enantiomer R) dissolved in 40 ml of an appropriate solvent, and stirred for about 1 hour. The resulting solid was filtrated, and washed with 8 ml of the appropriate solvent. The product was analyzed by XRD and HPLC, and the results are set forth in Table 1.

TABLE 1

| Example | Solvent | % yield | % R | XRD dry[1] | wet |
|---|---|---|---|---|---|
| 2 | n-BuOH | 48.5 | 0.96 | Ma2 | Ma2 |
| 3 | ethyl acetate | 80 | 0.40 | Ma2 | Ma2 |
| 4 | MTBE | 91 | 2.20 | Ma2 | Ma2 |
| 5 | water | 75 | 0.99 | Ma2 | Ma2 |

[1]Results obtained after drying in a vacuum oven (10 mm Hg) at 50° C. for 16 hours.

Examples 6-8

Maleic acid (1.5 g) was added to a solution of 4 g of DNT (2.30% enantiomer R) dissolved in 40 ml of an appropriate solvent, and the mixture was heated to reflux for about 10 minutes. After cooling to room temperature (except where is indicated), the mixture was stirred for an additional 1 hour, filtrated, and washed with 8 ml of the appropriate solvent. The results are described in Table 2:

TABLE 2

| Example | Solvent | % yield | % R | XRD dry[1] | wet |
|---|---|---|---|---|---|
| 6 | n-BuOH | 76 | 0.24 | Ma2 | Ma2 > Ma1 |
| 7 | ethyl acetate | 86 | 0.19 | Ma2 | Ma2 |
| 8[2] | acetone | 50 | 0.30 | Ma3 | Ma3 |

[1]Results obtained after drying in a vacuum oven (10 mm Hg) at 50° C. for 16 hours.
[2]Cooling to 4° C.

Example 9

Maleic acid (2 g) was added to a solution of 4 g of DNT (2.30% enantiomer R) dissolved in 40 ml of MTBE, and the mixture was heated to reflux for about 10 minutes. After cooling to room temperature, the mixture was stirred for an additional 1 hour, filtrated, and washed with 8 ml of MTBE. After drying in a vacuum oven (10 mm Hg) at 50° C. for 16 hours, 4.8 g (88% yield) of product were obtained. The product was analyzed by XRD and found to be Form Ma2 before, and, after drying, the level of the R-enantiomer found in the product was 2.26.

Example 10

Maleic acid (1.1 g) was added to a solution of 3 g of DNT (2.30% enantiomer R) dissolved in 40 ml of water, and the mixture was heated to reflux for about 10 minutes. After cooling to room temperature, the mixture was stirred for an additional 1 hour, filtrated, and washed with 8 ml of water. After drying in a vacuum oven (10 mm Hg) at 50° C. for 16 hours, 2.9 g (70% yield) of product were obtained, containing 0.19% of enantiomer R. The product was analyzed by XRD, and found to be Form Ma2 before and after the drying.

Example 11

Maleic acid (1.2 g) was added to a solution of 4 g of DNT (16% enantiomer R) dissolved in 40 ml of ethyl acetate heated to reflux. The mixture was maintained at reflux for about 10 minutes, cooled to room temperature, and stirred for an additional 1 hour. The resulting solid was filtrated, and washed with ethyl acetate. After drying in a vacuum oven (10 mm Hg) at 50° C. for 16 hours, 3.4 g (62% yield) of DNT-maleate were obtained containing 7.35% of enantiomer R.

Example 12

Maleic acid (0.2 g) was added to a solution of 0.67 g of DNT (7.35% enantiomer R) dissolved in 7 ml of ethyl acetate heated to reflux. The mixture was maintained at reflux for about 10 minutes, cooled to room temperature, and stirred for an additional 1 hour. The resulting solid was filtrated, and washed with ethyl acetate. After drying in a vacuum oven (10 mm Hg) at 50° C. for 16 hours, 0.74 g (80% yield) of DNT-maleate were obtained containing 1.04% of enantiomer R.

Example 13

Crystallization of DNT-maleate

Ten ml of ethyl acetate were heated to reflux, and slowly added to a mixture of 1 g of DNT-maleate (7.35% enantiomer R) in 10 ml of ethyl acetate until dissolution. The solution was cooled to room temperature, and stirred for an additional one and half hours. The resulting solid was filtrated, and washed with ethyl acetate. After drying in a vacuum oven (10 mm Hg) at 50° C. for 16 hours, 0.69 g (69% yield) of DNT-maleate were obtained containing 0.3% of enantiomer R.

Example 14

Crystallization of DNT-maleate

A mixture of 0.5 g of DNT-maleate (0.3% enantiomer R) in 10 ml of ethyl acetate was heated to reflux, and stirred for 3 hours. The solution was cooled to room temperature, and stirred for an additional one and half hours. The resulting solid was filtrated, and washed with ethyl acetate. After drying in a vacuum oven (10 mm Hg) at 50° C. for 16 hours, 0.47 g (94% yield) of DNT-maleate were obtained, having no detectable amounts of enantiomer R.

Example 15

Preparation of DNT

A 22 percent solution of ammonium hydroxide (1 ml) was added to a mixture of 1.5 g of DNT-maleate in 15 ml toluene and 15 ml water. The mixture is stirred at 25° C. for 20 to 30 minutes, the organic phase was separated and washed with water (3×30 ml), and the solution was evaporated to dryness to give 0.67 g of DNT.

Example 16

Preparation of DNT Oxalate

To a solution of 2.1 g of DNT-base (12% enantiomer R) dissolved in 12 ml of ethyl acetate was added a solution of 0.6 g of oxalic acid in 12 ml of ethyl acetate. The resulting mixture was stirred at room temperature for an hour, filtrated and washed with ethyl acetate. After drying, in a vacuum oven for overnight, 2 g (77% yield) of DNT-oxalate were obtained containing 12% of enantiomer R.

Example 17

A 100 ml three necked flask, equipped with mechanical stirrer, thermometer, dean stark, and condenser, was charged with 5 g of DNT and 25 ml of toluene. The clear solution was heated, and an azeotropic distillation was performed for about 30 to about 60 minutes. After cooling to room temperature, 4.6 ml of ethyl chloroformate were added during over a period of 1 to 2 hours, and the reaction mixture was stirred at room temperature over night.

Diluted NH₄OH was added to the reaction mixture, which was stirred for an additional 30 minutes. After phase separation, the organic phase was washed with water (3×20 ml), dried over Na₂SO₄, filtered, and concentrated to dryness to give 5.2 g of a brownish oil. (88% chemical yield).

Example 18

A 100 ml three necked flask equipped, with mechanical stirrer, thermometer, and condenser, was charged with 2.5 g duloxetine ethyl carbamate and 20 ml toluene. The mixture was stirred, and 4.8 g of KOH were added in portions, followed by reflux for about 3 hours.

After cooling, 30 ml of water, followed by 20 ml of toluene, were added, and the resulting organic phase was washed with water (3×20 ml), dried over Na₂SO₄, filtered and concentrated to dryness to give 1.70 g of an oily product. (85.31% yield).

Example 19

To a solution of 1 g of duloxetine in 10 ml MEK was slowly added 0.32 ml of a 37 percent hydrochloric acid solution. The mixture was stirred until a solid formed. The resulting solid was filtered, and dried in a vacuum oven to give 0.50 g of (S)-(+)-duloxetine hydrochloride. (94.64% yield).

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

What is claimed:

1. A compound (S)-N,N-dimethyl-3-(1-naphthalenyloxy)-3-(2-thienyl)propanamine maleate) having the following formula:

2. A composition comprising the compound of claim 1, wherein the compound is present in said composition with at least about 99.96% enantiomeric purity by HPLC.

3. A composition comprising the compound of claim 1, wherein the compound is present in said composition with at least about 95% enantiomeric purity by HPLC.

4. A composition comprising the compound of claim 1, wherein the compound is present in said composition with at least about 85% enantiomeric purity by HPLC.

5. A composition comprising the compound of claim 1, wherein the compound is present in said composition with at least about 50% enantiomeric purity by HPLC.

6. A composition comprising the compound of claim 1, wherein the R-enantiomer of DNT-maleate is undetectable by HPLC; wherein the detection limit for the HPLC method is 0.02%.

7. A crystalline form of (S)-N,N-dimethyl-3-(1-naphthalenyloxy)-3-(2-thienyl)-propanamine maleate):

characterized by a powder XRD pattern with peaks at about 9.4°, 14.0°, 18.7°, 23.3°, and 24.9° 2θ±0.2° 2θ.

8. The crystalline form of claim 7, further characterized by X-ray powder diffraction peaks at about 20.6°, 24.6°, and 24.9° 2θ±0.2° 2θ.

9. The crystalline form of claim 7, wherein the crystalline form is present in a batch at a polymorphic purity level of at least about 50% by weight.

10. A crystalline form of (S)-N,N-dimethyl-3-(1-naphthalenyloxy)-3-(2-thienyl)-propanaznine maleate):

characterized by a powder XRD pattern with peaks at about 14.4°, 18.5°, 23.1°, 27.2°, and 31.3° 2θ±0.2° 2θ.

11. The crystalline form of claim 10, further characterized by X-ray powder diffraction peaks at about 13.9°, 20.3°, and 26.3° 2θ±0.2° 2θ.

12. The crystalline form of claim 10, wherein the crystalline form is present in a batch at a polymorphic purity level of at least about 50% by weight.

13. A crystalline form of (S)-N,N-dimethyl-3-(1-naphthalenyloxy)-3-(2-thienyl)-propanamine maleate):

characterized by a powder XRD pattern with peaks at about 9.4°, 18.7°, 23.4°, and 25.3° 2θ±0.2° 2θ.

14. The crystalline form of claim 13, further characterized by X-ray powder diffraction peaks at about 14.0°, 20.6°, 24.9°, 28.1°, and 29.5° 2θ±0.2° 2θ.

15. The crystalline form of claim 13, wherein the crystalline form is present in a batch at a polymorphic purity level of at least about 50% by weight.

* * * * *